(12) United States Patent
Murase et al.

(10) Patent No.: US 9,087,616 B2
(45) Date of Patent: Jul. 21, 2015

(54) RADIATION PROTECTION DEVICE

(75) Inventors: Sosuke Murase, München (DE);
Barbara Ballsieper, München (DE)

(73) Assignee: MAVIG GMBH, Munich (DE)

( * ) Notice: Subject to any disclaimer, the term of this patent is extended or adjusted under 35 U.S.C. 154(b) by 0 days.

(21) Appl. No.: 13/989,235

(22) PCT Filed: Nov. 23, 2011

(86) PCT No.: PCT/EP2011/070790
§ 371 (c)(1),
(2), (4) Date: Jul. 31, 2013

(87) PCT Pub. No.: WO2012/069528
PCT Pub. Date: May 31, 2012

(65) Prior Publication Data
US 2013/0299723 A1 Nov. 14, 2013

(30) Foreign Application Priority Data

Nov. 24, 2010 (DE) .......................... 10 2010 061 893

(51) Int. Cl.
*G21F 3/00* (2006.01)
*A61B 6/10* (2006.01)
(Continued)

(52) U.S. Cl.
CPC . *G21F 3/00* (2013.01); *A61B 6/107* (2013.01); *A61B 6/032* (2013.01); *A61N 2005/1094* (2013.01)

(58) Field of Classification Search
CPC ..... A61N 2005/1094; G21F 3/00; A61B 6/10
See application file for complete search history.

(56) References Cited

U.S. PATENT DOCUMENTS 3,308,297 A    3/1967    Mansker
4,062,518 A  * 12/1977   Stivender et al. .......... 250/519.1
(Continued)

FOREIGN PATENT DOCUMENTS

CN        1653555 A    8/2005
DE      1 614 361 A    5/1970
(Continued)

OTHER PUBLICATIONS

Examination Report, dated Nov. 14, 2011, issued in corresponding German Patent Application No. DE 10 2010 061 893.4.
(Continued)

*Primary Examiner* — Michael Logie
*Assistant Examiner* — James Choi
(74) *Attorney, Agent, or Firm* — Scully, Scott, Murphy & Presser, PC

(57) ABSTRACT

A radiation protection device for shielding radiation emitted by a radiation source is provided. A first radiation protection panel of the device has a recess and a first through bore. A second radiation protection panel of the device is adjustable relative to the first panel in a way such that the recess can be covered by the second panel. The second panel has a second through bore. A connection element of the device is directly attached to a holding element. The connection element extends through both through bores. The second panel is directly attached to the connection element in a rotatable manner. The connection element, the first through bore and the second through bore are located at a center position of the first panel. The recess is dimensioned to receive a human arm.

12 Claims, 5 Drawing Sheets

(51) Int. Cl.
*A61N 5/10* (2006.01)
*A61B 6/03* (2006.01)

(56) References Cited

U.S. PATENT DOCUMENTS

| | | | | |
|---|---|---|---|---|
| 4,923,162 | A * | 5/1990 | Fleming et al. | 248/276.1 |
| 4,977,585 | A | 12/1990 | Boyd | |
| 6,627,891 | B1 * | 9/2003 | Warner et al. | 250/337 |
| 2003/0159194 | A1 * | 8/2003 | Frank | 2/102 |
| 2008/0031422 | A1 * | 2/2008 | Barkow et al. | 378/203 |
| 2008/0093568 | A1 * | 4/2008 | Fox et al. | 250/515.1 |
| 2010/0189432 | A1 * | 7/2010 | Viglione et al. | 396/468 |
| 2011/0174997 | A1 * | 7/2011 | Rees | 250/516.1 |
| 2013/0331691 | A1 * | 12/2013 | Uber et al. | 600/432 |

FOREIGN PATENT DOCUMENTS

| | | |
|---|---|---|
| DE | 20307606 U1 | 10/2003 |
| DE | 102004039411 A1 | 2/2006 |
| EP | 0 023 522 A1 | 2/1981 |
| GB | 2461569 A * | 1/2010 |
| WO | WO2007060561 A2 | 5/2007 |

OTHER PUBLICATIONS

Chinese Office Action and Chinese Search Report dated Nov. 24, 2014 issued in Application No. 201180056831.5 (in English and Chinese).

Japanese Office Action dated Mar. 17, 2015 issued in Patent Application No. 2013-540343 (in English and in Japanese).

* cited by examiner

RADIATION PROTECTION DEVICE

TECHNICAL FIELD

The invention relates to a radiation protection device which can be used for shielding radiation, in particular X-ray radiation, emitted from a radiation source, for example during a computer tomography.

STATE OF THE ART

In medicine as well as in various other technical fields, various kinds of imaging techniques are nowadays used for examining internal and external structures of an object, for example organs and structures of the human body. Among others, tomographic techniques such as computer tomography, sonography, magnetic resonance tomography, positron emission tomography or the like techniques are used as slice imaging techniques.

For example, computer tomography means the computer-aided evaluation of radiographs of an object, which were taken from different directions, wherein a three-dimensional image of the object and in particular also the interior thereof is generated. In computer tomography, X-rays are typically emitted in a well-directed manner so that they pass through an object and are recorded simultaneously by detectors. The evaluation of the emitted radiation intensity and the detected radiation intensity provides information as to the absorption of the X-rays by the object. In most cases, the degree of absorption is illustrated in gray values or in a colored manner and shown on a scale such as the Hounsfield scale. In a computer, the respective data are then analyzed and processed to sectional views or slices or series of sectional views or slices as well as three-dimensional images in any desired plane. Various kinds of tissues of the object can be recognized in the slices and views because each tissue has a specific gray level or color depending on its structure.

Tomographic techniques are nowadays used in particular in medicine also during interventions on the object, wherein the object and the interior thereof are continuously visualized during the intervention. This allows the surgeon or doctor to monitor the intervention optically and carry it out exactly without having to open the object accordingly. In this regard, interventions comprise, for example, puncturing of joints or organs for the purpose of diagnosis or therapy, drainage of interiors of the object and/or the human body and the like.

For a tomography procedure, various kinds of scanners or detectors are nowadays used, which typically have a tunnel into which the object to be examined is inserted at least partially. In the tunnel, the object is then exposed to radiation and analyzed. At least in the tunnel openings of such detectors there is often the risk that radiation having a relatively high intensity exits to the outside through the tunnel opening. This radiation can comprise primary radiation emitted directly by the scanner or the detector but also secondary radiation scattered by the object and emitted by it. Because of the effect of such radiation and in particular of X-ray radiation, which is known to be harmful to the health and which depends on the exposition duration and the radiation intensity, measures for protecting the surgeon or doctor from the radiation are normally taken, for example, during a computer tomography procedure. Protective clothing, which comprises a textile fabric or plastic material provided with a heavy metal such as lead, is often used for this purpose. Since the protective effect increases as the amount of heavy metal in the protective clothing increases, such protective clothing is typically relatively heavy, which impairs the surgeon's mobility and increases his/her physical load. In particular in connection with the mentioned interventions, also the mobility of the surgeon can be important. Moreover, apron-like protective clothing is often used, which does not cover the entire body so that specific areas of the body such as the shoulders or the head and especially the particularly radiosensitive eyes are not protected.

As an alternative or in addition to the mentioned protective clothing, nowadays various additional radiation protection devices are known. For example, U.S. Pat. No. 4,977,585 A shows an X-ray scanner having a tunnel for introducing a patient into the scanner and shielding curtains at both openings of the tunnel. The shielding curtains can flexibly cover the openings up to the patient and comprise lead or brass embedded therein. Thus, the radiation of the scanner can be shielded towards the outside. Since, however, it is not intended that the surgeon accesses the interior of the tunnel with his/her hands without opening or moving the shielding curtains, interventions of the above-mentioned kind are possible with this X-ray scanner only with a relatively strong impairment of the protective effect of the shielding curtains. Moreover, also the visibility into the interior of the X-ray scanner is restricted by the shielding curtains, which can complicate the surgeon's interventions.

Furthermore, for example WO 2007/060561 A1 discloses a radiation shield for a tomographic scanner. The radiation shield has the shape of a cylinder segment and can be swiveled around the scanner so that it can be arranged between the scanner and a surgeon while the patient is irradiated by the scanner. The radiation shield is made from a radiation-dampening, optically transparent material such as a plastic material containing lead. Thus, the surgeon can see the patient and the scanner while the radiation shield is arranged between him/her and the scanner and he/she is protected by the radiation shield. However, the surgeon cannot access the patient when being protected by the radiation shield, so that for interventions of the above-mentioned kind, he/she must open the radiation shield and is thus no longer protected against the radiation of the scanner.

Therefore, it is the object of the present invention to suggest a radiation protection device which can protect a surgeon also during an intervention.

ILLUSTRATION OF THE INVENTION

In accordance with the present invention, the object is achieved by a radiation protection device as defined in independent claim 1. Advantageous embodiments of the radiation protection device according to the present invention can be taken from the dependent claims.

The gist of the invention is as follows: A radiation protection device for shielding radiation, in particular X-ray radiation, emitted from a radiation source comprises a first radiation protection panel having at least one recess and a second radiation protection panel which is adjustable relative to the first radiation protection panel in such a way that at least one recess can be covered by the second radiation protection panel. In this connection, the radiation source is, for example, the radiation source of a detector or a scanner of a tomography procedure and in particular the X-ray radiation source of a computer tomographic scanner (CT scanner). In this connection, the radiation protection panel relates, for example, to a component which is substantially planar and dampens the emitted radiation and thus protects the environment at its one side from the radiation present at its other side. The second radiation protection panel can be adjustable relative to the first radiation protection panel in that it can be moved substantially linearly, wherein the surfaces of the first and second radiation protection panels are preferably arranged so as to be parallel to one another. Alternatively, the second radiation protection panel is substantially rotatable relative to the first radiation protection panel, wherein the surfaces of the first and second radiation protection panels are arranged so as to be parallel to one another. The at least one recess can, for example, extend from an edge of the first radiation protection panel into the radiation protection panel. The recess can alternatively be realized as a through opening or hole. In particular, the recess can be dimensioned such that a surgeon can put one or more finger(s), one or both hand(s) or one or both arm(s) through it.

During a tomography procedure, the radiation protection device of the present invention can be arranged in different ways between a surgeon and a scanner and thus protect the surgeon from the radiation emitted by the scanner. In particular, it can be arranged in front of an opening of a tunnel of the scanner into which an object to be imaged, such as a patient or a particular part of his/her body, can be inserted. The opening of the tunnel can thus be substantially covered in the direction of the surgeon. Since the at least one opening can be selectively opened and closed, the surgeon can at the same time reach through the opened at least one recess while being protected against the radiation source by the radiation protection device. In this way, the radiation protection device ensures that, for example, an intervention can be performed on the object to be imaged and the surgeon is at the same time protected by the radiation protection device. If the intervention is ended at least temporarily, the at least one recess can again be covered by the second radiation protection panel. In this way, the surgeon is in each case relatively well protected against the emitted radiation, while access to the object is nevertheless possible at all times.

Preferably, the second radiation protection panel is configured and adjustable relative to the first radiation protection panel in such a manner that either one or two or more recess(es) present in the first radiation protection panel can be covered by means of the second radiation protection panel. Such a configuration of the second radiation protection panel ensures that a plurality of recesses in the first radiation protection panel are selectively accessible and that the radiation protection device nevertheless comprises relatively few components. The radiation protection device can thus be configured in a relatively simple, cost-efficient and robust manner.

Alternatively, the first radiation protection panel comprises at least two recesses, and at least two second radiation protection panels are provided, which are adjustable relative to the first radiation protection panel, so that one of the at least two recesses can be covered by means of a respective second radiation protection panel. Such an embodiment ensures that also a plurality of recesses in the first radiation protection panel are selectively accessible and that the radiation protection device can be operated relatively easily.

Alternatively, the radiation protection device comprises a rotational fixation for adjusting the at least one second radiation protection panel relative to the first radiation protection panel about a rotational axis, wherein a plurality of second radiation protection panels are preferably adjustable about a common rotational axis. Such a rotational fixation ensures a relatively simple robust construction of the radiation protection device.

The radiation protection device preferably comprises a moving device for moving at least one of the second radiation protection panels relative to the first radiation protection panel. A moving device of this kind can be realized for linear movement of the at least one of the second radiation protection panels and ensures that the at least one recess of the first radiation protection panel can be opened and closed relatively easily.

According to a further aspect of the invention, the first radiation protection panel comprises a rectangular surface, wherein preferably the corners of the rectangular surface are rounded and wherein particularly preferably a first pair of diagonally opposite corners has a first curvature and a second pair of diagonally opposite corners has a further curvature, wherein the first curvature has preferably a larger radius than the further curvature. Preferably, the second pair of corners has a second and a third curvature, wherein the second curvature has a larger radius than the third curvature. A radiation protection panel which is shaped in this manner ensures that on the one hand no sharp-edged corners are present and that on the other hand the space required for the rotation of the first radiation protection panel is relatively small. Moreover, the embodiment comprising the corners with the first curvature can be designed in accordance with the curvature of an opening of a tunnel of a scanner, so that it can preferably cover this opening and, if necessary, can be inserted at least partially into the opening. Typical diameters of such tunnels are approx. 70 cm or approx. 80 cm, i.e. the corresponding radius is approx. 35 cm or approx. 40 cm. The radius of the first curvature is preferably equal to or smaller than the radius of a tunnel. Thus, during the irradiation, the radiation protection device can be variably placed at the object or the patient, so that a relatively simple intervention is possible. The second radiation protection panel preferably has a rectangular surface which is smaller than the rectangular surface of the first radiation protection panel, wherein preferably one side of the surface is at least partially inclined and wherein the surface and shape of the second radiation protection panel are adapted to the respective recess in the first radiation protection panel which should be covered. The second radiation protection panel is preferably configured and arranged at the first radiation protection panel in such a manner that at one side it forms a continuous outer edge with the edge of the first radiation protection panel and at its other sides projects from the edge of the recess to be covered if the second radiation protection panel closes the recess. Because of the at least partially inclined realization of the second radiation protection panel, material can be saved when manufacturing the second radiation protection panel without impairing its covering properties. With such a realization of the second radiation protection panel, a preferred operability and an effective shielding effect can be achieved.

Preferably, the radiation protection device comprises a connection element for attachment to a holding element, wherein the holding element can be attached preferably to a stationary means in a room or to an examination device or to a support of an examination table. Such a holding element ensures a stable fixation of the radiation protection device and allows a flexible positioning with preferable degrees of mobility. In this case, the second radiation protection panel is preferably attached to the connection element in a rotatable manner.

According to a further aspect of the invention, the first radiation protection panel and the second radiation protection panel are made from a transparent material, preferably from lead acrylic glass. Such a transparent realization of the radiation protection device ensures that a surgeon can visually control the object during the irradiation in a protected manner and in particular can perform interventions on this object.

BRIEF DESCRIPTION OF THE DRAWINGS

In the following, the radiation protection device according to the present invention will be described in more detail with reference to the enclosed drawings on the basis of embodiments, wherein.

EMBODIMENTS OF THE INVENTION

Figure 1:
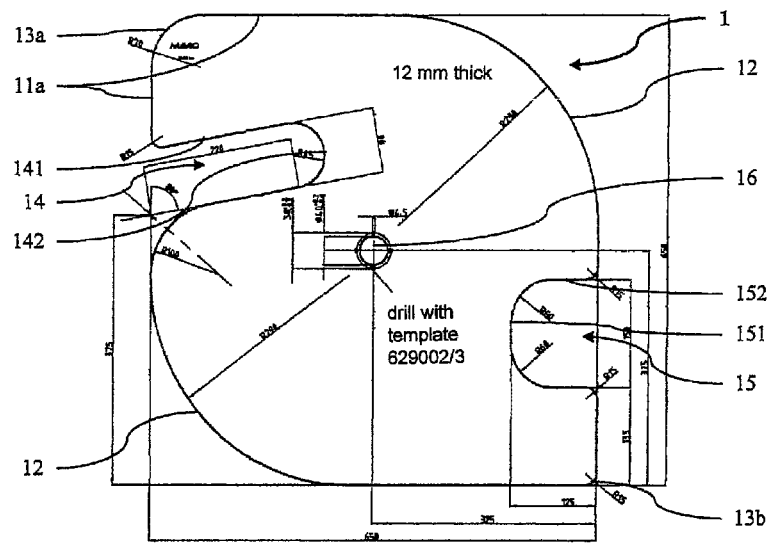
FIG. 1 shows a schematic top view of a first radiation protection panel of a first embodiment of a radiation protection device according to the invention.

In the following description, specific expressions are used for practical reasons and should not be understood as being restrictive. The terms "right", "left", "at the bottom" and "at the top" are directions in the drawing referred to. The expressions "inwardly" and "outwardly" are directions towards and away from the geometrical center of the radiation protection device as well as respective parts thereof. The terminology comprises the terms explicitly mentioned above, derivations thereof and terms having a similar meaning.

FIG. 1 shows a radiation protection panel 1 of a first embodiment of a radiation protection device according to the invention. The first radiation protection panel 1 is manufactured from lead acrylic glass as a substantially rectangular or square plate having a thickness of, e.g., 12 mm, wherein the four corners are each rounded. It has four sides 11 which, without the rounded corners, have a length of, e.g., approx. 650 mm. A first pair of diagonally opposite corners of the four corners has a first curvature 12 and a second pair of opposite corners of the four corners has second and third curvatures 13a and 13b. The first curvature 12 has a radius of, e.g., approx. 290 mm which is larger than that of the second curvature 13a, which has a radius of, e.g., approx. 70 mm, and that of the third curvature 13b, which has a radius of approx. 15 mm.

Starting at one of its sides 11 (at the left top of FIG. 1), the first radiation protection panel 1 comprises a first inwardly extending recess 14, and starting at a side 11 opposite said side 11 (at the right bottom of FIG. 1) it comprises a second recess 15. The first recess 14 is substantially rectangular with sides 141 having a length of, e.g., approx. 220 mm and a width of, e.g., approx. 90 mm, wherein the sides 141 are connected with each other towards their inner end through a bend 142 having a radius of, e.g., approx. 45 mm. The second recess 15 is also substantially rectangular with sides 151 having a length of, e.g., approx. 150 mm and a bend 152 having a length of, e.g., approx. 125 mm. Each of the transitions from the side 151 to the bend 152 is rounded.

In its center, the first radiation protection panel 1 comprises a stepped through bore 16 having a first diameter of, e.g., approx. 50 mm and a second diameter of, e.g., approx. 40 mm. Each of the transitions from the sides 11 of the first radiation protection panel 1 to the first recess 14 and to the second recess 15 is rounded.

Both the first recess 14 and the second recess 15 are dimensioned such that, e.g., a human arm can reach through them. Preferably, the first recess is adapted to the diameter of a forearm of a surgeon and the second recess to the diameter of an upper arm of a surgeon. During operation, the first radiation protection panel 1 can preferably be arranged in front of an opening of a tunnel of a scanner for, e.g., a computer tomography. Because of the design of the first radiation protection panel 1, which is adapted to the geometry of the tunnel, which typically has a diameter of approx. 700 mm or approx. 800 mm, and in particular to its width and radius of curvature, the radiation protection panel 1 can preferably be arranged in various positions in front of the opening of the tunnel and at least partially also inside the tunnel. The design of the first radiation protection panel 1 thus can enable a surgeon to position the first radiation protection panel 1, in accordance with the intended intervention, in such a manner that, on the one hand, he/she can comfortably and precisely reach through the recesses and, on the other hand, he/she is protected by the first radiation protection panel 1 from a radiation source of the scanner.

For the entire further description, the following holds true. If a Figure comprises reference signs for the purpose of illustrative clarity, but if said reference signs are not mentioned in the directly corresponding description text, reference is made to the discussion thereof in the previous description of the Figures. Moreover, if reference signs are mentioned in the description text directly relating to a Figure, but if said reference signs are not shown in the corresponding Figure, reference is made to the previous Figures.

Figure 2:
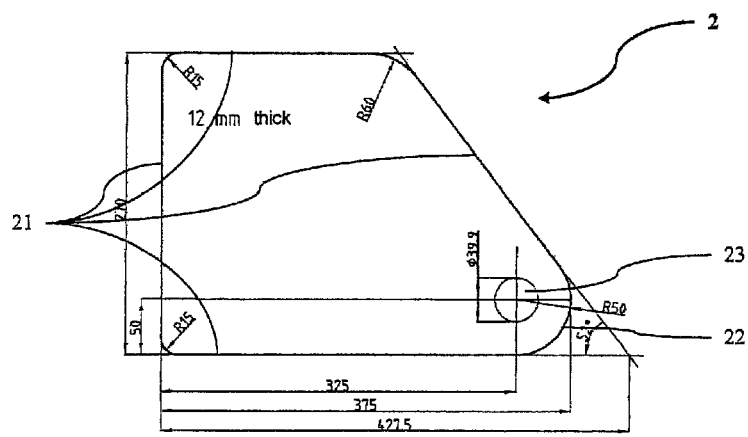
FIG. 2 shows a schematic top view of a second radiation protection panel of the radiation protection device of FIG. 1.

FIG. 2 shows a second radiation protection panel 2 of the first embodiment of a radiation protection device according to the invention. The second radiation protection panel 2 is made from lead acrylic glass as a substantially plate-shaped rectangle having a partly inclined longitudinal side, i.e. as a plate-shaped rectangular trapezoid, having a thickness of, e.g., approx. 12 mm, wherein each of the four corners is rounded. It has four sides 21 and it has a height of, e.g., approx. 270 mm as well as a length of, e.g., approx. 375 mm. In the area of the acute angle of the second radiation protection panel 2, which has a curvature 22 with a radius of, e.g., approx. 50 mm, the second radiation protection panel 2 comprises a through bore 23 having a diameter of, e.g., approx. 39.9 mm.

Figure 3:
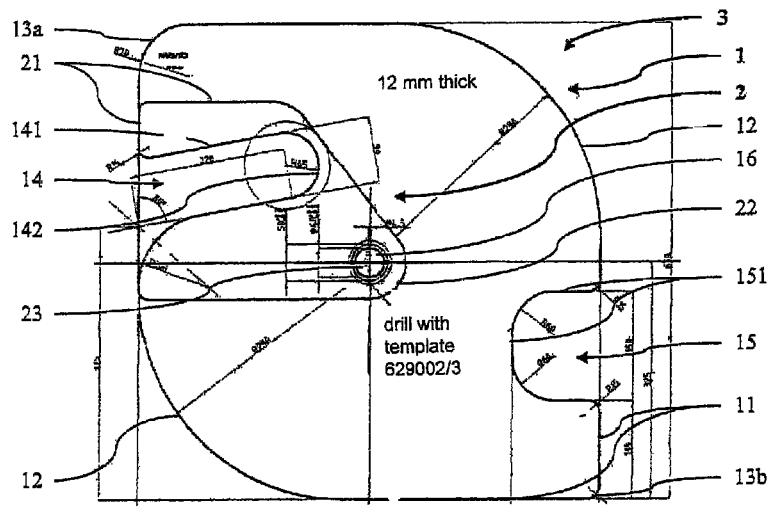
FIG. 3 shows a schematic top view of the radiation protection device of FIG. 1 and of FIG. 2 with the second radiation protection panel being arranged on the first radiation protection panel.

FIG. 3 shows the first radiation protection panel 1 and the second radiation protection panel 2 of the radiation protection device 3 on top of each other. The stepped bore 16 of the first radiation protection panel 1 adjoins the bore 23 of the second radiation protection panel 2 so that they define together a common rotational axis or a common center of rotation. In the position shown in FIG. 3, the second radiation protection panel 2 is moved or rotated such that it completely covers the first recess 14 of the first radiation protection panel 1 so that said recess 14 is not accessible. In this position, however, the second recess 15 of the first radiation protection panel 1 is not covered by the second radiation protection panel 2 and is completely accessible.

During operation, the second radiation protection panel 2 can be adjusted relative to the first radiation protection panel 1 by rotating it about the axis of rotation. It can be selectively arranged such that it covers either the first recess 14 of the first radiation protection panel 1, the second recess 15 of the first radiation protection panel 1 or none of the recesses of the first radiation protection panel 1. Thus, in accordance with his/her requirements, the surgeon can keep either one of the two or also both recesses 14, 15 of the first radiation protection panel 1 open so that he/she can reach through the recesses of the radiation protection device 3, for example for the intervention on the object to be scanned.

Figure 4:
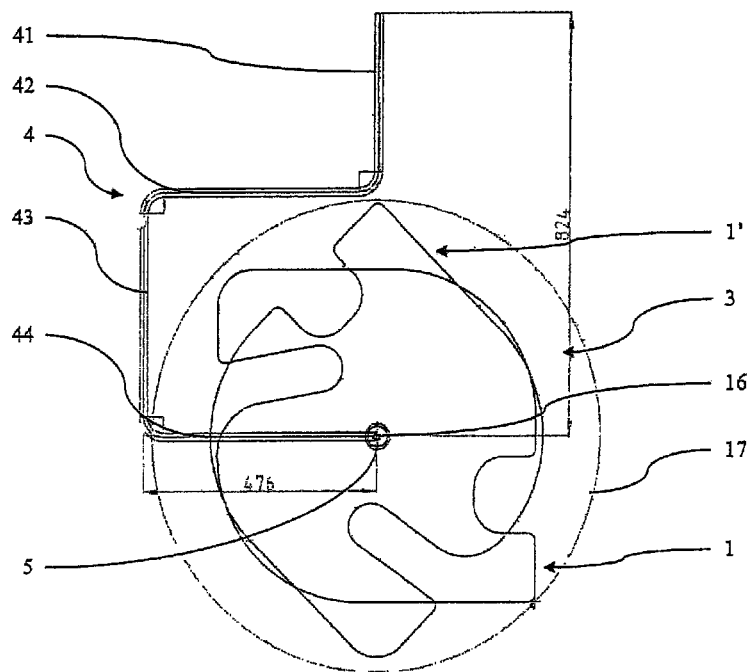
FIG. 4 shows a schematic view of a holding element and of the first radiation protection panel of the radiation protection device of FIG. 1 being attached thereto by means of a ball joint.

FIG. 4 shows the radiation protection device 3 which is connected to a holding element 4 in a rotational and swiveling manner via a ball joint 5 as connection element and rotational fixation. The second radiation protection panel 2 of the radiation protection device is not shown in FIG. 4. The holding element 4 has a first portion 41 which, for example, can be connected to a support arm and, for example, can be mounted by means of said support arm to the ceiling of a room, a stationary means in the room, an examination device or a support of an examination table. Via a bent right angle, the first portion 41 makes a transition into the second portion 42, which is arranged at a right angle with respect to the first portion 41. The second portion 42 makes a transition into a third portion 43, likewise via a bent right angle, and the third portion 43 makes a transition into a fourth portion 44, likewise via a bent right angle. Therefore, the first portion 41 and the third portion 43 as well as the second portion 42 and the fourth portion 44 are arranged in parallel with respect to each other. At the same time, the second portion 42 and the fourth portion 44 are arranged at a right angle with respect to the first portion 41 and the third portion 43. The second portion 42, the third portion 43 and the fourth portion 44 have a length of, e.g., approx. 475 mm.

At its longitudinal end facing away from the third portion 43, the fourth portion 44 is connected with the first radiation protection panel 1 via the ball joint 5. The ball joint comprises a bolt extending through the bore 16 of the first radiation protection panel 1. The first radiation protection panel is preferably firmly connected to the bolt and, by means of the ball joint, can be brought in any desired rotational and swiveling position. The first radiation protection panel can alternatively be attached around the rotational axis defined by the bore 16 or the bolt of the ball joint passing through it in the plane of its surface in a rotatable manner. For the purpose of illustration, the radiation protection panel 1 is shown in FIG. 4 in two rotational positions. The illustration of the radiation protection panel 1 is rotated such that the first recess 14 lies at a left side 11 and the second recess 15 lies at a right side 11. The four sides 11 are arranged substantially horizontally at the top and bottom as well as vertically at the left and right. The illustration of the radiation protection panel 1' is rotated such that the opposite corners of the four sides 11 substantially extend upwardly or downwardly and to the left and right. The first recess 14 lies at a right bottom side and the second recess 15 at a left top side 11. The corners of the first radiation protection panel 1 describe a circumference of rotation 17 which determines the maximum space required by the first radiation protection panel 1 as well as the minimum length of the third portion 43 and the fourth portion 44 of the holding element 4. Since the first radiation protection panel 1 has rounded corners, the circumference of rotation 17 can be kept relatively small.

Moreover, the second rotation protection panel 2 is preferably attached in a rotatable manner to the bolt of the ball joint 5. The bolt projects through the bore 23 in the second rotation protection panel 2. The bolt has portions with different diameters corresponding to the respective diameters of the bore 16 in the first radiation protection panel 1 and the bore 23 in the second radiation protection panel 2. The length of the portions of the bolt substantially corresponds to the respective thickness of the first and second radiation protection panels. Preferably, the distance between the two radiation protection panels is small in the thickness direction, i.e. perpendicularly with respect to their surfaces, and preferably ranges between 0.1 mm to 1 mm.

The holding element 4 can preferably be mounted so as to be rotatable about the first portion 41. Moreover, the first radiation protection panel 1 can be arranged so as to be tiltable about the fourth portion 44 of the holding element 4. Due to this design of the holding element 4 and the first radiation protection panel 1, the radiation protection device 3 can be arranged by the surgeon variably in a suitable position.

Figure 5:
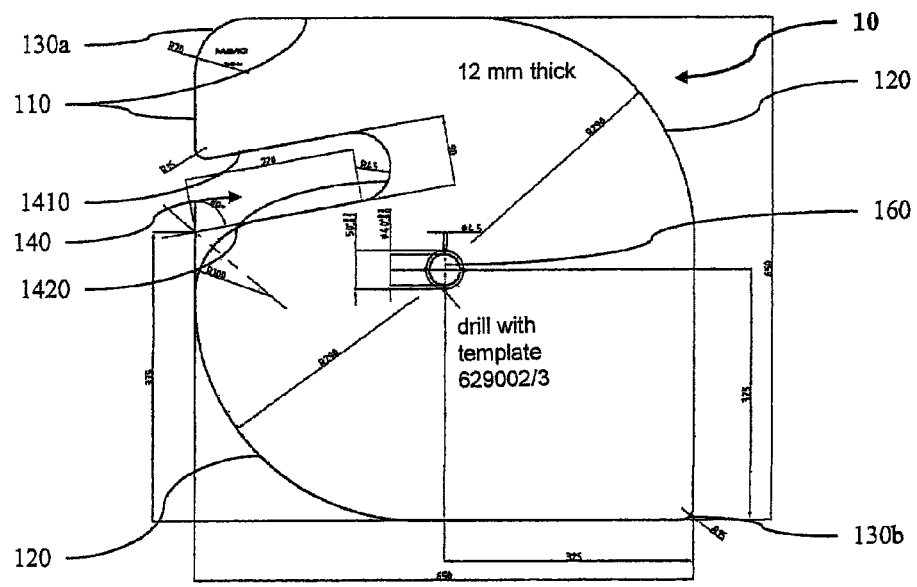
FIG. 5 shows a schematic top view of a first radiation protection panel of a second embodiment of a radiation protection device according to the invention.

FIG. 5 shows a radiation protection panel 10 of a second embodiment of a radiation protection device according to the invention. The first radiation protection panel 10 is designed in a manner similar to the first radiation protection panel 1 of FIG. 1 to FIG. 4, but it only comprises one recess. In particular, the radiation protection panel 10 comprises four sides 110, two opposite corners with a curvature 120 having a larger radius than two other opposite corners with curvatures 130 having a smaller radius, and a central stepped bore 160. Furthermore, the first recess 160 extends inwardly from the left side 110 of the radiation protection panel 10. The recess has two opposite, substantially parallel sides 1410 and a bend 1420 which connects both sides and forms the end of the recess. The distance between both sides is preferably adapted to the diameter of a forearm of a surgeon. The ratio of the length of the recess to the distance between both sides preferably ranges between 1:1 to 3:1.

Figure 6:
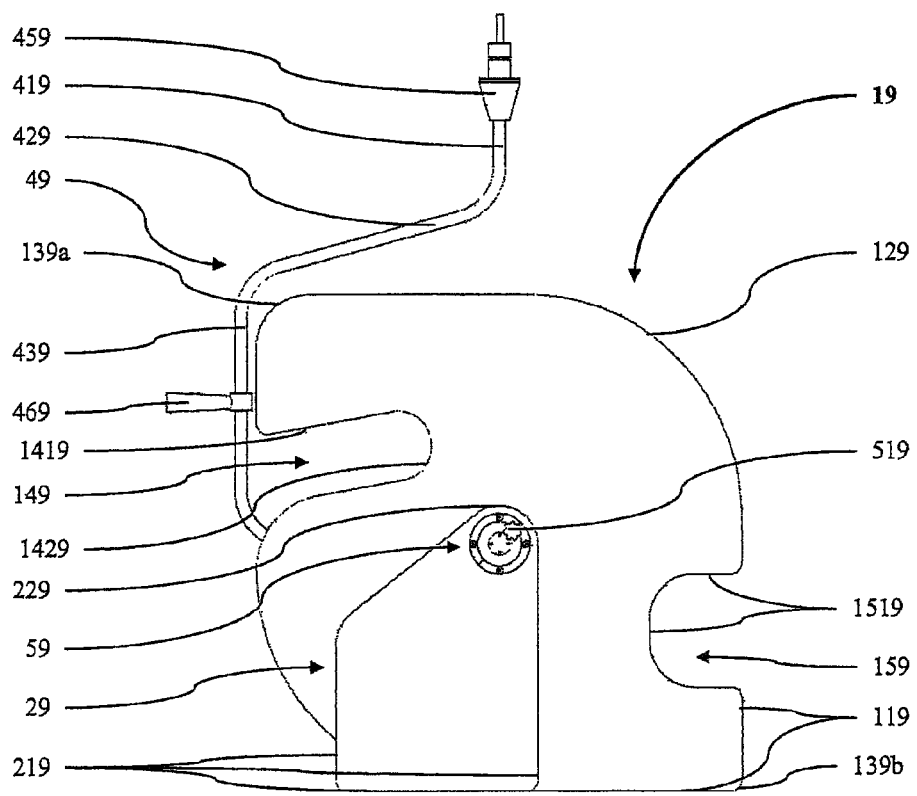
FIG. 6 shows a schematic top view of a third embodiment of a radiation protection device according to the invention being fixed to a holding element.
Figure 7:
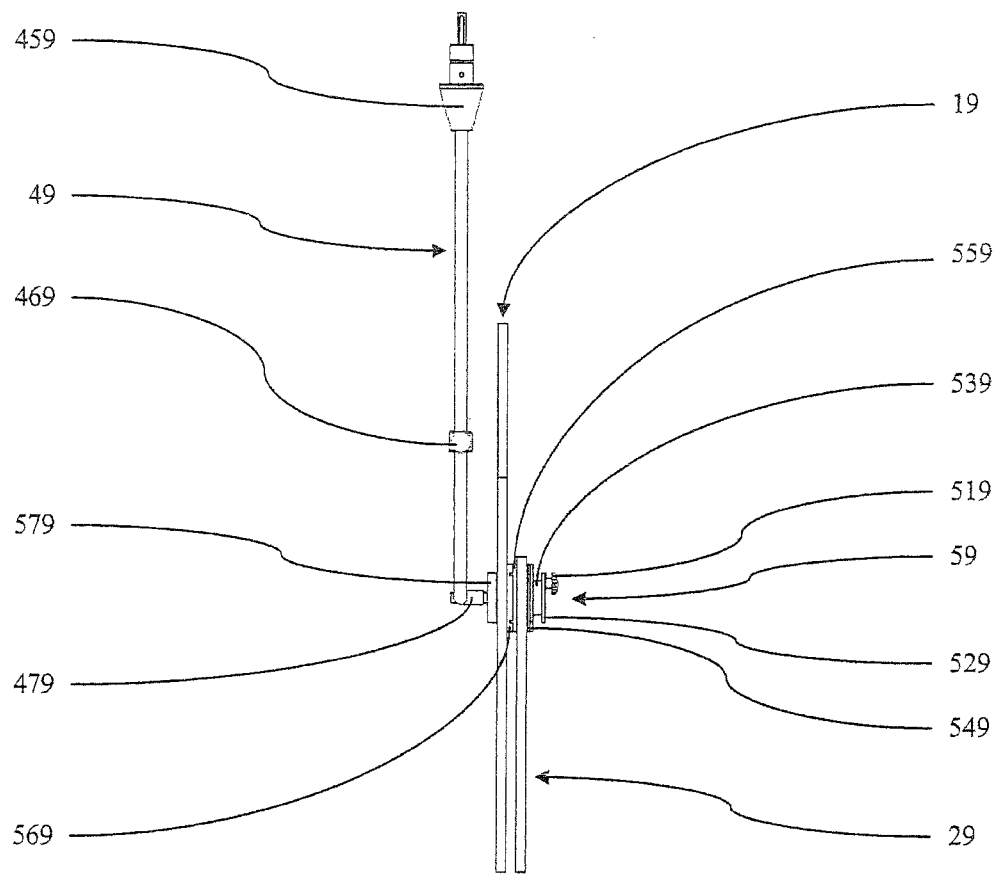
FIG. 7 shows a schematic side view of the radiation protection device of FIG. 6.
Figure 8:
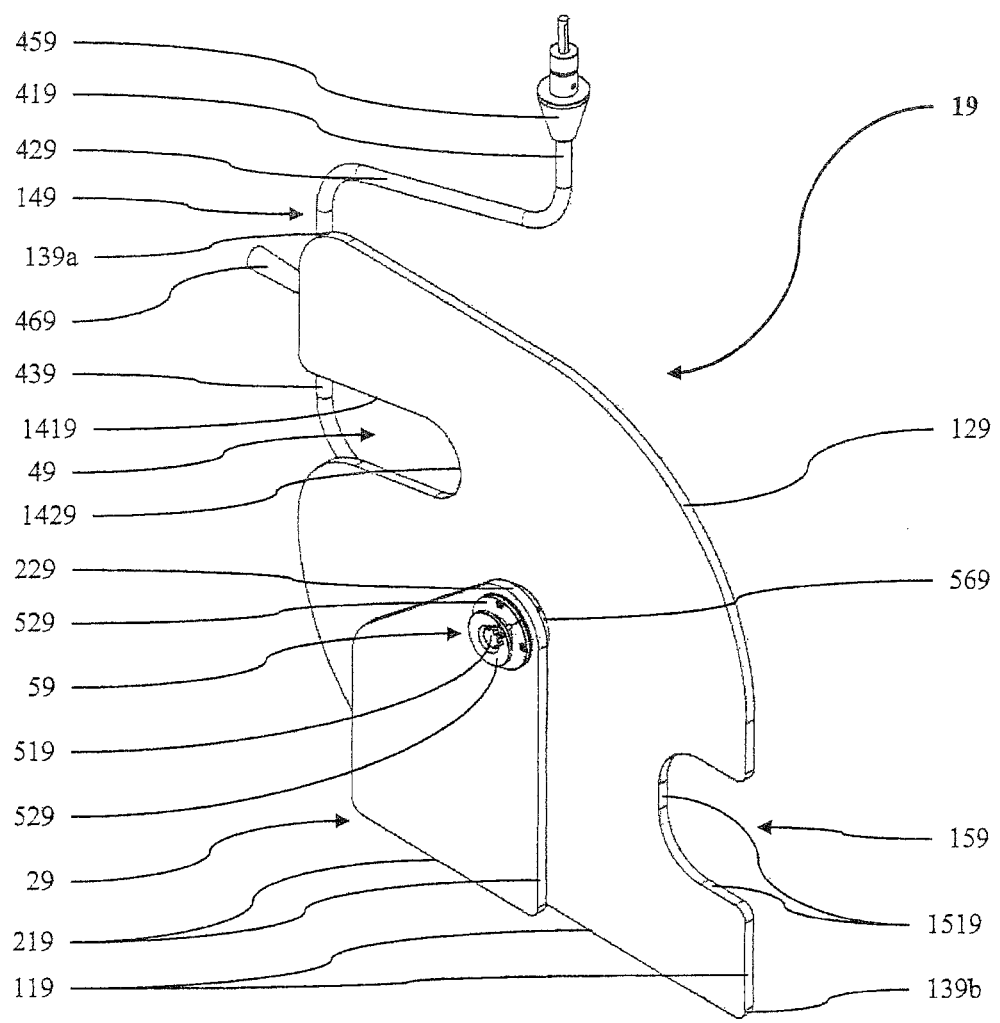
FIG. 8 shows a perspective view of the radiation protection device of FIG. 6.

FIG. 6, FIG. 7 and FIG. 8 show a third embodiment of a radiation protection device according to the invention, which is fixed to a holding element 49. The radiation protection device comprises a first radiation protection panel 19 whose structure substantially corresponds to that of the above-mentioned first radiation protection panel 1 of the first embodiment of the radiation protection device according to the invention, and a second radiation protection panel 29 whose structure substantially corresponds to that of the above-mentioned second radiation protection panel 2 of the first embodiment of a radiation protection device according to the invention. Accordingly, the first radiation protection panel 19 is manufactured as a substantially rectangular or square plate having four sides 119, wherein each of the four corners is rounded. A first pair of diagonally opposite corners of the four corners comprises a first curvature 129 and a second pair of diagonally opposite corners of the corners comprises second and third curvatures 139*a* and 139*b*. The first curvature 129 has a larger radius than the second curvature 139*a* and the third curvature 139*b*. Starting at one of its sides 119 (at the left in FIG. 6), the radiation protection panel 19 comprises a first inwardly extending recess 149 and starting at a side 119 opposite to this side 119 (at the right in FIG. 6) a second recess 159. The first recess 149 is substantially rectangular and has longitudinal sides 1419, wherein the sides 1419 are connected with each other towards their inner end by means of a bend 1429. The second recess 159 is also substantially rectangular and has sides 1519. Each of the transitions of the sides 1519 is rounded. Each of the transitions from the sides 119 of the first radiation protection panel 19 to the first recess 149 and to the second recess 159 is rounded.

The second radiation protection panel 29 is substantially manufactured as a plate-shaped rectangle having a partially inclined longitudinal side, i.e. as a plate-shaped right-angled trapezoid, having four sides 219, wherein each of the four corners is rounded. In the area of the acute angle of the second radiation protection panel 29, which has a curvature 229, the second radiation protection panel 29 is connected in a rotatable manner to the first radiation protection panel 19 by means of a mounting structure 59 with a knurled screw 519. Via the mounting structure 59, the first radiation protection panel 19 and the second radiation protection panel 29 are at the same time also connected to a holding element 49. The holding element 49 comprises an adapter 459 by means of which it can be mounted to a support arm. It comprises a first portion 419 which adjoins the adapter 459 and which makes a transition via a bent obtuse angle into an inclined second portion 429. The second portion 429 also makes a transition via a bent obtuse angle into a third portion 439, which in turn makes a transition via a bent obtuse angle into a fourth portion 449. An actuating handle 469 is attached to the third portion 439 of the holding element 49 so that the surgeon can position and adjust the radiation protection device 19.

FIG. 7 shows a side view of the radiation protection device with its first radiation protection panel 19 and its second radiation protection panel 29, wherein, i.a., the mounting structure 59 is shown in more detail. The mounting structure 59 comprises a cylindrical piston 539 which extends through the through bore of the second radiation protection panel 29 and the through bore of the first radiation protection panel 19. At an axial longitudinal end of the piston 539 facing away from the holding element 49 (at the right in FIG. 7), a flange portion 529 adjoins the piston 539 and projects from the piston 539 in the radially outward direction. The mounting structure 59 further comprises a first, a second, a third and a fourth ring disk or washer 549, 559, 569 and 579 through which the piston 539 extends. The second radiation protection panel 29 is arranged between the first washer 549 and the second washer 559 and connected in a stationary manner with these two washers. Analogously, the first radiation protection panel 19 is arranged between the third washer 569 and the fourth washer 579 and connected in a stationary manner with these two washers.

The mounting structure 59 is mounted to a mounting portion 479 of the holding element 49. In the position shown in FIG. 7, the knurled screw 519 presses the first washer 549 together with the second radiation protection panel and the second washer 559 against the first radiation protection panel 19, so that the first radiation protection panel 19 and the second radiation protection panel 29 are connected with each other in a non-rotating manner.

For predetermining possible rotational positions of the second radiation protection panel 29 relative to the first radiation protection panel 19, the second washer 559 comprises catches extending in the direction of the third washer 569. The third washer 569 comprises respective recesses into which the catches of the second washer 559 engage. For rotating the second radiation protection panel 29 relative to the first radiation protection panel 19, the knurled screw 519 is released and the second radiation protection panel 29 is moved on the piston 539 away from the first radiation protection panel 19 until the catches of the second washer 559 have been moved out of the recesses of the third washer 569. The stop provided by the flange portion 529 of the mounting structure 59 prevents the second radiation protection panel 29 from being demounted unintentionally. The released second radiation protection panel 29 can then be rotated in various positions so that it covers, as desired, the first recess 149, the second recess 159 or none of the recesses of the first radiation protection panel 19. In this position, there is enough space between the large and the small panel, so that a user can enter the space with his/her hand and the panels can be cleaned more easily.

Once the second radiation protection panel 29 has been rotated as desired, it is again moved on the piston 539 in the direction of the first radiation protection panel 19 until the catches of the second washer 559 engage in the recesses of the third washer 569. By tightening the knurled screw 519, the first radiation protection panel 29 is held in this position and connected with the second radiation protection panel 19 in a non-rotating manner.

Although the invention has been illustrated and described in detail on the basis of the Figures and the corresponding description, this illustration and this detailed description should be illustrative and exemplary and should not restrict the invention. It is a matter of fact that experts may make changes and modifications without leaving the scope and the gist of the following claims. In particular, the invention also comprises embodiments comprising any combination of features that are mentioned or shown above or below in connection with various embodiments. For example, the invention can also be realized by the following further structural variations:

The radiation protection device can also comprise a plurality of second radiation protection panels. In particular, the embodiment of the radiation protection device shown in FIG. 1 to FIG. 4 can also comprise a second radiation protection panel, which can correspond to the first second radiation protection panel. Thus, both recesses of the first radiation protection panel can be covered at the same time.

The peripheral ends of the first radiation protection panel can comprise connection means such as snap fasteners to which further radiation protection means can be attached, if required. Therefore, if required, a gap located, e.g., below the first radiation protection panel can be covered by means of, e.g., a protection curtain in a simple and flexible manner.

The invention also comprises individual features in the Figures, even if they are shown therein in connection with other features and/or if they are not mentioned above or below. Furthermore, individual ones of the alternative embodiments or alternative features which are described in the Figures and in the description can be excluded from the subject-matter of the invention.

Moreover, the term "comprising" and derivations thereof do not exclude other elements or steps. Furthermore, the indefinite articles "a" and "an" and derivations thereof do not exclude a plurality. The functions of several features mentioned in the claims can be fulfilled by a unity. The terms "substantially", "about", "approximately" and the like in connection with a property or a value define in particular also exactly the property or exactly the value. All the reference signs in the claims are not meant as restricting the scope of the claims.

The invention claimed is:

1. A radiation protection device for shielding radiation emitted by a radiation source, comprising:
   a first radiation protection panel, wherein the first radiation protection panel comprises at least one recess and a first through bore,
   at least one second radiation protection panel, which is adjustable relative to the first radiation protection panel in such a way that the at least one recess can be covered by the second radiation protection panel, the at least one second radiation protection panel comprising a second through bore, and
   a connection element directly attached to a holding element, wherein the connection element extends through both the first through bore and the second through bore, wherein the second radiation protection panel is directly attached to the connection element in a rotatable manner;

wherein the connection element, the first through bore, and the second through bore are located at a center position of the first radiation protection panel; and wherein the recess is dimensioned to receive a human arm.

2. The radiation protection device according to claim 1, wherein the second radiation protection panel is configured and adjustable relative to the first radiation protection panel in such a way that by means of the second radiation protection panel selectively either one or two or more of the recesses present in the first radiation protection panel can be covered.

3. The radiation protection device according to claim 1, wherein the first radiation protection panel comprises at least two recesses and at least two second radiation protection panels are provided, which are adjustable relative to the first radiation protection panel in such a way that by means of a respective second radiation protection panel one of the at least two recesses can be covered.

4. The radiation protection device according to claim 1, comprising a rotational fixation for adjusting the at least one second radiation protection panel relative to the first radiation protection panel about a rotational axis, wherein a plurality of second radiation protection panels are adjustable about a common rotational axis.

5. The radiation protection, device according to claim 1, comprising a moving device by means of which at least one of the second radiation protection panels can be moved relative to the first radiation protection panel.

6. The radiation protection device according to claim 1, wherein the first radiation protection panel has a rectangular surface, wherein the corners of the rectangular surfaces are rounded.

7. The radiation protection device according to claim 6, wherein the second radiation protection panel has a rectangular surface which is smaller than the rectangular surface of the first radiation protection panel, wherein one side of the surface of the second protection panel is at least partially inclined and wherein the surface and shape of the second radiation protection panel are adapted to the respective recess in the first radiation protection panel which should be covered, and the second radiation protection panel extends beyond the edge of the recess to be covered.

8. The radiation protection device according to claim 1, wherein the holding element can be attached to a stationary means in a room or to an examination device or to a support of an examination table.

9. The radiation protection device according to claim 1, wherein the first radiation protection panel and the second radiation protection panel are made from a transparent material.

10. The radiation protection device according to claim 1, wherein said radiation is X-ray radiation.

11. The radiation protection device according to claim 6, wherein said rectangular surface has a first pair of diagonally opposite corners having a first curvature, and a second pair of diagonally opposite corners having a second and a third curvature, wherein the first curvature has a larger radius than the second and third curvatures.

12. The radiation protection device according the claim 9, wherein said transparent material is lead acrylic glass.

\* \* \* \* \*